United States Patent
Li et al.

(10) Patent No.: US 9,926,618 B2
(45) Date of Patent: Mar. 27, 2018

(54) EXTRACTING AGENT FOR SEPARATING LITHIUM ISOTOPES AND USE THEREOF

(71) Applicant: Shanghai Institute of Organic Chemistry, Chinese Academy of Sciences, Shanghai (CN)

(72) Inventors: Beili Li, Shanghai (CN); Huaiyu Sheng, Shanghai (CN); Jinbo Hu, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 302 days.

(21) Appl. No.: 14/440,473

(22) PCT Filed: May 8, 2013

(86) PCT No.: PCT/CN2013/075340
§ 371 (c)(1),
(2) Date: May 4, 2015

(87) PCT Pub. No.: WO2014/067278
PCT Pub. Date: May 8, 2014

(65) Prior Publication Data
US 2015/0299822 A1 Oct. 22, 2015

(30) Foreign Application Priority Data
Nov. 5, 2012 (CN) .......................... 2012 1 0437155

(51) Int. Cl.
| | | |
|---|---|---|
| C22B 26/00 | (2006.01) | |
| C22B 26/12 | (2006.01) | |
| B01D 59/24 | (2006.01) | |
| B01D 11/04 | (2006.01) | |
| C07D 221/12 | (2006.01) | |
| C07F 1/02 | (2006.01) | |
| C22B 7/00 | (2006.01) | |

(52) U.S. Cl.
CPC .......... *C22B 26/12* (2013.01); *B01D 11/0492* (2013.01); *B01D 59/24* (2013.01); *C07D 221/12* (2013.01); *C07F 1/02* (2013.01); *C22B 7/006* (2013.01); *Y02P 20/582* (2015.11)

(58) Field of Classification Search
CPC ....... C22B 26/12; C22B 7/006; C07D 221/12; B01D 11/0492; B01D 59/24
USPC .................................. 423/2, 179.5; 252/184
See application file for complete search history.

(56) References Cited

FOREIGN PATENT DOCUMENTS

| | | | |
|---|---|---|---|
| CN | 102430338 A | | 5/2012 |
| JP | 01-184027 | * | 7/1989 |
| KR | 2012-0031771 A | | 4/2012 |

OTHER PUBLICATIONS

Chen, Chinese Journal of Rare Materials, 1983, vol. 2, pp. 79-87.
Chen et al., Studies on separation of lithium isotopes by solvent extraction, I. The separation effects of lithium isotopes by sudan I-neutral ligand synergetic extraction systems, Atomic Energy Science and Technology, 1987, vol. 21, No. 4, 8 pages.
Jiang et al., Isotopic Effect of a Chemical Exchange System Featuring Li-Crown Ether Complex, Atomic Energy Science and Technology, 1986, vol. 20, No. 1, 7 pages.
Palko et al., Lithium isotope separation factors of some two-phase equilibrium systems, The Journal of Chemical Physics, 1976, v64, No. 4, pp. 1828-1837.
Xiao et al., Present Status and Future Prospect of Isotope Separation(II), J. of Nuclear and Radiochemistry, 1991, v13, No. 1, 11 pages.
Xu et al., Green and efficient extraction strategy to lithium isotope separation with double ionic liquids as the medium and ionic associated agent, J. Radioanal Nucl Chem, 2013, v295, pp. 2103-2110.

* cited by examiner

*Primary Examiner* — Steven Bos
(74) *Attorney, Agent, or Firm* — Wolf, Greenfield & Sacks, P.C.

(57) ABSTRACT

The present invention discloses an extracting agent for separating lithium isotopes and an organic extraction phase containing the extracting agent; the organic extraction phase easily enriches $^7$Li and achieves the separation of lithium isotopes. The present invention also discloses a high-efficiency method for separating lithium isotopes in an aqueous solution, in which the organic extraction phase of the present invention is used, said organic extraction phase being suitable for single-stage and multi-stage extraction processes.

9 Claims, 1 Drawing Sheet

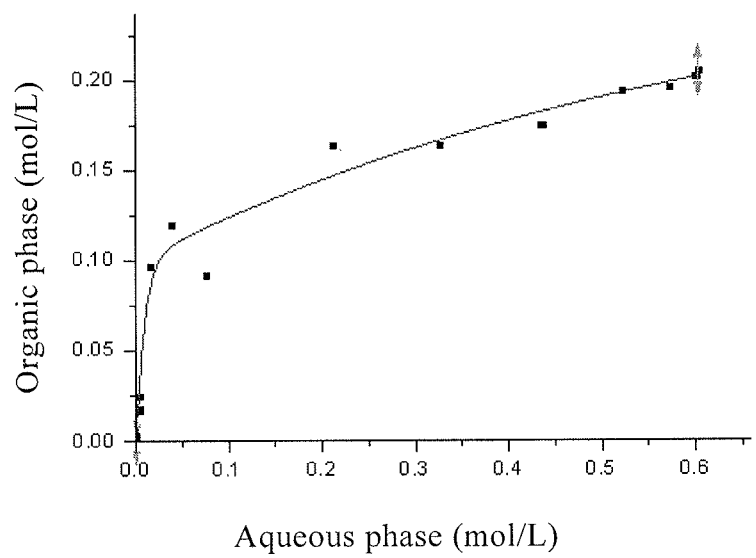

EXTRACTING AGENT FOR SEPARATING LITHIUM ISOTOPES AND USE THEREOF

RELATED APPLICATIONS

This application is a national stage filing under 35 U.S.C. 371 of International Application PCT/CN2013/075340 entitled "EXTRACTING AGENT FOR SEPARATING LITHIUM ISOTOPES AND USE THEREOF" filed May 8, 2013, which claims priority to CN Application No. 201210437155.2, filed Nov. 5, 2012, the entire disclosure of each of which is incorporated by reference herein in its entirety.

TECHNICAL FIELD

The present invention relates to the field of chemical engineering and, in particular, to a benzoquinoline extractant for separating lithium isotope and the use thereof.

BACKGROUND OF THE INVENTION

There are a number of natural isotopes of lithium (Li), in which the abundances of $^7$Li and $^6$Li are the highest, which are 92.48% and 7.52%, respectively. The two isotopes play important roles in nuclear material field; nevertheless, their nuclear reaction properties are quite different. $^7$Li is an indispensible molten salt coolant in thorium-based molten salt reactors. Since the thermal neutron absorption cross section of $^6$Li is quite high (up to 941 barns), while that of $^7$Li is only 0.033 barns, the molten salt reactors require >99.995% abundance of $^7$Li. Meanwhile, highly purified $^7$Li is usually used to adjust the pH value of primary coolant in pressurized-water reactors; and it is also used as a heat-conducting heat carrier agent in fusion reactors. Furthermore, the tritium which is of quite low abundance in nature can be produced by using neutron to irradiate $^6$Li (n, α) T nuclear reaction. $^6$Li is a fuel in nuclear fusion reactors, wherein the abundance of $^6$Li should be >30%.

Either thorium-based molten salt reactors or nuclear fusion reactors will provide a solution for the development of strategic new energies in China. Therefore, lithium isotopes being an indispensable strategic material, the development of processes for separating lithium isotopes and the development and manufacture of new lithium isotope extractants have always been the research hotspots, while at the same time they are also the technological obstacles of the field.

Currently, existing methods for separating lithium isotopes comprise electromagnetic method, molecular distillation, electro-migration, electrolysis and various kinds of chemical exchange methods (Xiaoan Xiao et al, *Journal of Nuclear and Radiochemistry,* 1991, 13, 1).

So far, most of the lithium isotope separating methods only remain in the laboratory research stage (Yaohuan Chen, *Chinese Journal of Rarematerials,* 1983, 2, 79). For example, neutral solvent extraction system (e.g. isoamylol/ LiBr system), ion exchange system (e.g. hexanoic acid/ kerosene system), chelating system (e.g. sudan I-TOPO system), etc., all have a comparatively low separation coefficient α (usually <1.010), and therefore cannot be used in industrialized extraction processes (Yaohuan Chen, *Atomic Energy Science and Technology,* 1987, 21, 433). The extractant reported in CN201110425430.4 has a low extraction rate (the one-time extraction rate is only 16%), and the hydrophilic ionic liquids are expensive and difficult to be recycled through phase inversion; furthermore, the extractant has not be used in multiple stage enrichment and separation experiments. The systems like crown ether and cryptand extraction systems enriched $^6$Li in organic phase. Although the separation coefficient α is comparatively high, the system is difficult to synthesize, has a high cost and high toxicity, and it also did not accomplish multiple stage extraction to enrich lithium isotopes (Yanlin Jiang et al, *Atomic Energy Science and Technology,* 1986, 20, 1).

At present, lithium amalgam chemical exchange method can satisfy the technical requirements for isotope separation, and has become the only method for industrial production of lithium isotopes (Palko, A, A, et al. *J. Chem. Phys,* 1976, 64, 1828). However, lithium amalgam method requires a large amount of mercury, which is severely harmful to operators as well as the environment. Moreover, since lithium amalgam method is easy to enrich $^6$Li, and lithium amalgam will gradually decompose in the extraction column, it is not suitable for the separation processes which have multiple stages and require high $^7$Li abundance (>99.99%).

Therefore, there is an urgent need in the art for an extractant which is safe, environment friendly, efficient, suitable for multiple stage enrichment and separation, and easy to enrich $^7$Li.

SUMMARY OF THE INVENTION

The purpose of the present invention is to provide an extractant for separating lithium isotopes, which is safe, environment friendly, efficient, stable, suitable for multiple stage enrichment and separation, and easy to enrich $^7$Li, as well as the use thereof.

In the first aspect of the present invention, it provides an extraction organic phase for separating lithium isotopes, said extraction organic phase comprising: a diluent and the compound of formula (I) used as an extractant;

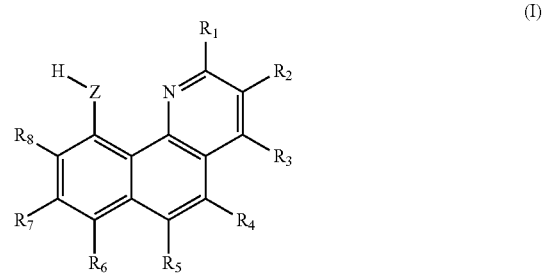

wherein,

Z is oxygen atom, sulfur atom, or nitrogen atom substituted by $R^9$, wherein $R^9$ is hydrogen, $C_{1-6}$ alkyl-sulfonyl, $C_{1-6}$ haloalkyl-sulfonyl, benzenesulfonyl, or $C_{1-6}$ alkyl-benzenesulfonyl;

$R^1$, $R^2$, $R^3$, $R^4$, $R^5$, $R^6$, $R^7$ and $R^8$ are independently hydrogen, $C_{1-6}$ alkyl, $C_{1-6}$ haloalkyl, $C_{2-6}$ alkenyl, $C_{2-6}$ alkynyl, $C_{1-6}$ alkoxy, $C_{3-6}$ cycloalkyl, halogen or phenyl.

In a preferred embodiment, said $R^9$ is hydrogen, trifluoromethanesulfonyl, methylsulfonyl or p-toluenesulfonyl.

In a preferred embodiment, $R^1$ is hydrogen, $C_{1-6}$ alkyl, $C_{1-6}$ haloalkyl or phenyl.

In a preferred embodiment, the extraction organic phase further comprises a synergic extractant.

In a preferred embodiment, the synergic extractant is phosphorus-containing compounds, nitrogen-containing compounds, alkyl quaternary sulfonium salt compounds or sulfoxide compounds.

In a preferred embodiment, the synergic extractant is neutral phosphorus-containing compounds, quaternary ammonium salt compounds, long-chain alkyl quaternary sulfonium salt compounds or neutral sulfoxide compounds.

In a preferred embodiment, the synergic extractant comprises: tributyl phosphate (TBP), trioctyl-phosphine oxide (TOPO), dibutyl butanephosphonate (DBBP), butyl dibutylphosphate (BDBP), methylene tetrabutyldiphosphate, trioctyl ammonium oxide, 1,10-phenanthroline, quaternary ammonium salt N263, dimethyl bis(N-octadecyl) ammonium chloride, methyldioctylsulfonium chloride or dioctyl sulfoxide.

In a preferred embodiment, the diluent comprises: kerosene, octanone, chloroform, carbon tetrachloride, toluene, dimethylbenzene, diethylbenzene, bromobenzene, anisole, nitromethane, 2-methyl cyclohexanone, methyl isobutyl ketone, chlorobenzene, dichlorobenzene, trichlorobenzene, diphenyl ether, or the combinations thereof.

In a preferred embodiment, the extraction organic phase further comprises lithium ions.

In a preferred embodiment, the content of lithium ions in the extraction organic phase is 0-2.0 mol/L; preferably 0.01-0.5 mol/L.

In the second aspect of the present invention, it provides use of the extraction organic phase of the first aspect of the present invention, wherein it is used in a process to separate $^7Li$ and $^6Li$.

In the third aspect of the present invention, it provides a system for separating lithium isotopes, said system comprising the extraction organic phase of the first aspect of the present invention, and an alkaline aqueous phase containing lithium ions.

In a preferred embodiment, the alkaline aqueous phase containing lithium ions is a water solution comprising a lithium salt and a strong alkali.

In a preferred embodiment, the lithium salt comprises LiCl, LiBr, LiI, $Li_2SO_4$, $Li_2CO_3$, $LiNO_3$, $Li_3PO_4$, LiSCN, $CF_3COOLi$ or LiOH; and/or the strong alkali comprises sodium hydroxide or potassium hydroxide.

In the fourth aspect of the present invention, it provides use of the system of the third aspect of the present invention, wherein it is used in a process for separating $^7Li$ and $^6Li$.

In a preferred embodiment, the process for separating lithium isotopes is to separate lithium isotopes from alkaline aqueous phase containing lithium ions.

In a preferred embodiment, said process is counter-current extraction process.

In a preferred embodiment, the counter-current extraction process is a multiple stage counter-current extraction process or single stage counter-current extraction process.

In a preferred embodiment, the multiple stage counter-current extraction process is a 2-600 stage counter-current extraction process; preferably is a 2-300 stage counter-current extraction process; more preferably is a 2-150 stage counter-current extraction process.

In the fifth aspect of the present invention, it provides a lithium ion chelate, said lithium ion chelate comprising: a synergic extractant, lithium ions, and the compound of formula (I) used as an extractant;

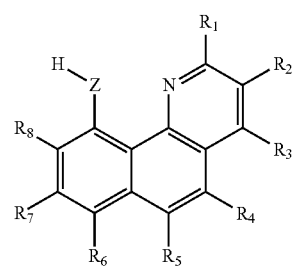
(I)

Wherein,

Z is oxygen atom, sulfur atom, or nitrogen atom substituted by $R^9$ (Z is O, S or $NR^9$), wherein $R^9$ is hydrogen, $C_{1-6}$ alkyl-sulfonyl, $C_{1-6}$ haloalkyl-sulfonyl, benzenesulfonyl or $C_{1-6}$ alkyl-benzenesulfonyl;

$R^1$, $R^2$, $R^3$, $R^4$, $R^5$, $R^6$, $R^7$ and $R^8$ are independently hydrogen, $C_{1-6}$ alkyl, $C_{1-6}$ haloalkyl, $C_{2-6}$ alkenyl, $C_{2-6}$ alkynyl, $C_{1-6}$ alkoxy, $C_{3-6}$ cycloalkyl, halogen or phenyl.

In a preferred embodiment, the lithium ion chelate is of formula (IIa) or formula (IIb):

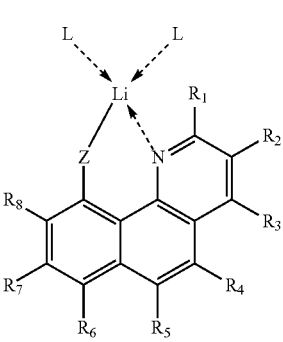
(IIa)

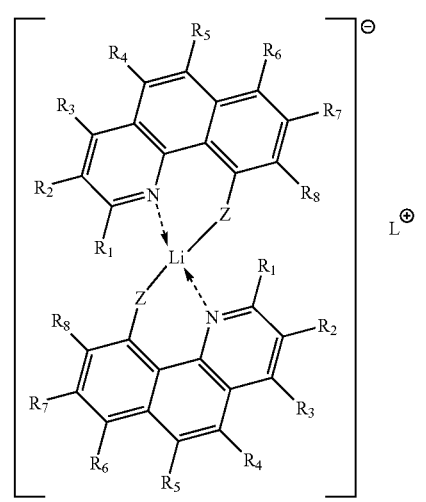
(IIb)

wherein the definitions of Z, $R^1$, $R^2$, $R^3$, $R^4$, $R^5$, $R^6$, $R^7$ and $R^8$ are as above, and L is a synergic extractant.

In a preferred embodiment, said $R^9$ is hydrogen, trifluoromethanesulfonyl, methylsulfonyl or p-toluenesulfonyl.

In a preferred embodiment, $R^1$ is hydrogen, $C_{1-6}$ alkyl, $C_{1-6}$ haloalkyl or phenyl.

In a preferred embodiment, the synergic extractant is phosphorus-containing compounds, nitrogen-containing compounds, alkyl quaternary sulfonium salt compounds or sulfoxide compounds.

In a preferred embodiment, the synergic extractant comprises: tributyl phosphate (TBP), trioctyl-phosphine oxide (TOPO), dibutyl butanephosphonate (DBBP), butyl dibutylphosphate (BDBP), methylene tetrabutyldiphosphate, trioctyl ammonium oxide, 1,10-phenanthroline, quaternary ammonium salt N263, dimethyl bis(N-octadecyl) ammonium chloride, methyldioctylsulfoniumate chloride or dioctyl sulfoxide.

In the sixth aspect of the present invention, it provides a method for separating lithium isotopes from alkaline aqueous phase containing lithium ion, said method comprising:

(1) Extracting:
(1.1) providing an extraction organic phase of the first aspect of the present invention;
(1.2) providing an alkaline aqueous phase containing lithium ion;
(1.3) mixing the extraction organic phase in step (1.1) and the alkaline aqueous phase in step (1.2), and then stratifying, and collecting the organic phase, said organic phase comprising the lithium ion chelate of the present invention;
(2) Reverse Extracting:
Reverse extracting the organic phase obtained from the above steps by using a reverse extractant, and collecting the aqueous phase to obtain the separated lithium isotopes.

In a preferred embodiment, the ratio of the extraction organic phase and the alkaline aqueous phase in step (1.3) is 1-10: 1-3 by volume.

In a preferred embodiment, the method is used to separate $^7$Li and $^6$Li.

In a preferred embodiment, the separated lithium isotope is $^7$Li.

In a preferred embodiment, the alkaline aqueous phase containing lithium ion is a water solution comprising a lithium salt and a strong alkali.

In a preferred embodiment, the lithium salt comprises LiCl, LiBr, LiI, $Li_2SO_4$, $Li_2CO_3$, $LiNO_3$, $Li_3PO_4$, LiSCN, $CF_3COOLi$ or LiOH.

In a preferred embodiment, the strong alkali comprises sodium hydroxide or potassium hydroxide.

In a preferred embodiment, the reverse extractant comprises a water solution containing NaCl, NaBr, NaI, $NH_4Cl$, $(NH_4)_2SO_4$, $Na_2SO_4$, $NaNO_3$, $NH_4NO_3$, KCl, or $K_2SO_4$.

In the seventh aspect of the present invention, it provides an extractant for separating lithium isotops, which has formula (I):

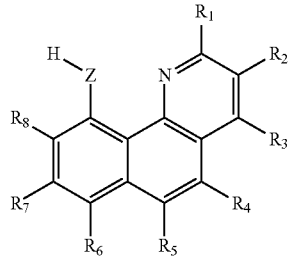

(I)

Wherein,
Z is oxygen atom, sulfur atom, or nitrogen atom substituted by $R^9$, wherein $R^9$ is hydrogen, $C_{1-6}$ alkyl-sulfonyl, $C_{1-6}$ haloalkyl-sulfonyl, benzenesulfonyl or $C_{1-6}$ alkyl-benzenesulfonyl;

$R^1$, $R^2$, $R^3$, $R^4$, $R^5$, $R^6$, $R^7$ and $R^8$ are independently hydrogen, $C_{1-6}$ alkyl, $C_{1-6}$ haloalkyl, $C_{2-6}$ alkenyl, $C_{2-6}$ alkynyl, $C_{1-6}$ alkoxy, $C_{3-6}$ cycloalkyl, halogen or phenyl;

With a proviso that the extractant is not the following compound:

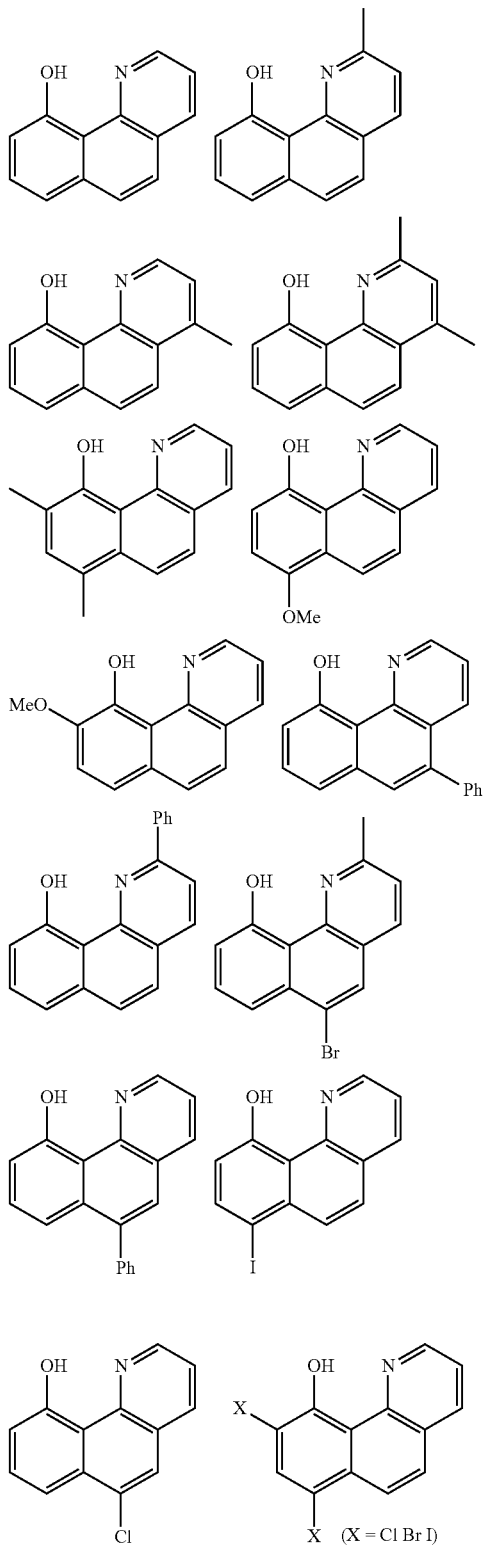

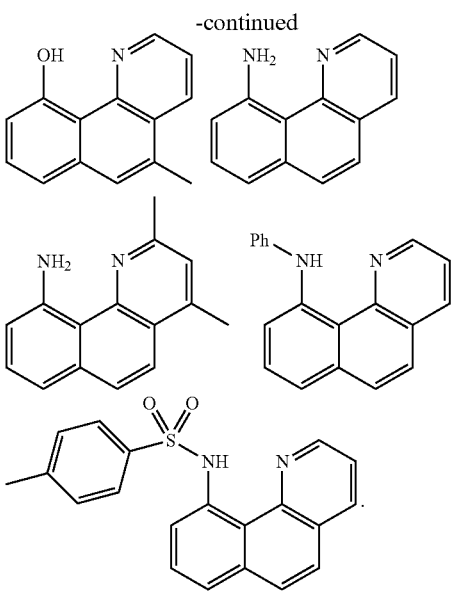

The benzoquinoline extractant of the present invention has achieved the environment friendly, efficient, multiple stage enrichment and separation of lithium isotopes.

The extractant, and the extraction organic phase which comprises the extractant, synergic extractant and diluent have achieved highly efficient extraction of lithium ions from water solutions; the organic phase is easy to enrich $^7$Li; the isotope exchange reaction during the extraction process is very quick; the extraction rate is high, with a high distribution ratio D value and a high separation coefficient α value; the extractant is of good chemical stability and thus amiable for reverse extraction and recycle, and it shows excellent performance in the multiple stage enrichment and extraction process of lithium isotopes.

It should be understood that, in the present invention, each of the technical features specifically described above and below (such as those in the Examples) can be combined with each other, thereby constituting new or preferred technical solutions which need not be specified again herein.

DESCRIPTION OF THE DRAWINGS

FIG. 1 is the extraction balance line of example 8.

EMBODIMENTS FOR CARRYING OUT THE INVENTION

Through long-term and intensive research, the inventor has unexpectedly discovered a benzoquinoline extractant. Said extractant can form a "extractant-lithium chelate" with lithium ion through the substituent group on its $10^{th}$ position (Z—H). The extractant can be used in the processes for separating lithium isotopes to effectively enrich $^7$Li, and it has a very high single stage separation coefficient and distribution ratio. The present invention is completed on this basis.

Terms

As used herein, the term "$C_{1-6}$ alkyl" refers to a linear or branched alkyl which has 1-6 carbon atoms, such as methyl, ethyl, propyl, isopropyl, butyl, isobutyl, sec-butyl, tert-butyl, or similar groups.

The term "$C_{2-6}$ alkenyl" refers to a linear or branched alkenyl which has 2-6 carbon atoms, such as ethenyl, allyl, 1-propenyl, isopropenyl, 1-butenyl, 2-butenyl, or similar groups.

The term "$C_{2-6}$ alkynyl" refers to a linear or branched alkynyl which has 2-6 carbon atoms, such as ethynyl, propynyl, and the like.

The term "$C_{3-6}$ cycloalkyl" refers to cyclopropyl, cyclobutyl, cyclopentyl, cyclohexyl, cycloheptyl, and the like.

The term "$C_{1-6}$ alkoxy" refers to a linear or branched alkoxy which has 1-6 carbon atoms, such as methoxy, ethoxy, propoxy, isopropoxy, butoxy, isobutoxy, sec-butoxy, tert-butoxy, or similar groups.

The term "$C_{1-6}$ alkoxy" refers to a linear or branched alkoxy which has 1-6 carbon atoms, such as methoxy, ethoxy, propoxy, isopropoxy, butoxy, isobutoxy, sec-butoxy, tert-butoxy, or similar groups.

The term "halogen" refers to fluorine, chlorine, bromine, or iodine. The term "halogenated" refers to groups substituted by one or more identical or different halogen atoms listed above, such as monofluoro methyl, trifluoromethyl, pentafluoroethyl, or similar groups.

Distribution Ratio and Separation Coefficient

In chemical exchange methods for separating lithium isotopes, the isotope exchange reaction between the two liquid phases can be expressed as follows:

$$^7LiA + {^6LiB} \rightleftharpoons {^7LiB} + {^6LiA}$$

Wherein A and B represents different coordination environment of lithium ions in two phases, such as organic phase and aqueous phase.

Distribution ratio (D value) represents the concentration distribution ratio of the total amount of the lithium ions in two phases:

$$D = \frac{[LiB]}{[LiA]} = \frac{[^7LiB] + [^6LiB]}{[^7LiA] + [^6LiA]}$$

i.e., one-time extraction rate $= \dfrac{[LiB]}{[LiA]+[LiB]} \times 100\% = \dfrac{D}{D+1} \times 100\%$ If B represents the extraction organic phase of the present invention and A represents aqueous phase, then the distribution ratio (D value) is the ratio between the total concentration of lithium ions in the organic phase and the total concentration of lithium ions in the aqueous phase, which varies with different experimental conditions (e.g., concentration of the extract, pH of the solution, concentration of the extractant, the nature of the diluent, etc.). The extraction ratio is the percentage of the total amount of lithium ions extracted into the organic phase to the total amount of lithium ions in the two phases, and it represents the completeness of extraction. The bigger the distribution ratio, the higher the extraction rate.

The separation coefficient of isotopes (a value) represents the effect of single stage separation of lithium isotopes, i.e., the quotient of the abundance ratio of the lithium isotopes in phase B to the abundance ratio of the lithium isotopes in phase A:

$$\alpha = \frac{[^7LiB]/[^6LiB]}{[^7LiA]/[^6LiA]}$$

The separation coefficient represents the separation degree of two substances by a certain unit separation operation or a certain separation procedure. The value of the separation coefficient reflects how difficult the separation of two substances is. When the separation coefficient is 1, the separation cannot be achieved; the more the separation coefficient deviates from 1, the easier the separation is.

As a preferred lithium isotope separation system, it should meet the following requirements in the process of chemical exchange:

(1) High distribution ratio (D value), i.e. the extraction rate is high;
(2) High isotope separation coefficient (a value);
(3) The isotope exchange reaction is sufficiently quick when two phases contact to each other;
(4) Lithium isotope can be easily reverse extracted, and achieve multi-stage enrichment and extraction;
(5) The chemical structure of the extractant is stable and economically practical.

Extractant

The extractant of the present invention is benzoquinoline derivatives, which is of formula (I):

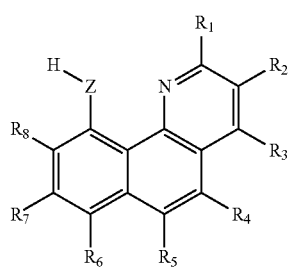
(I)

wherein,

Z is oxygen atom, sulfur atom, or nitrogen atom substituted by $R^9$ (Z is O, S or $NR^9$), wherein $R^9$ is hydrogen, $C_{1-6}$ alkyl-sulfonyl (i.e. sulfonyl substituted by $C_{1-6}$ alkyl), $C_{1-6}$ haloalkyl-sulfonyl, benzenesulfonyl or $C_{1-6}$ alkyl-benzenesulfonyl;

$R^1$, $R^2$, $R^3$, $R^4$, $R^5$, $R^6$, $R^7$ and $R^8$ are independently hydrogen, $C_{1-6}$ alkyl, $C_{1-6}$ haloalkyl, $C_{2-6}$ alkenyl, $C_{2-6}$ alkynyl, $C_{1-6}$ alkoxy, $C_{3-6}$ cycloalkyl, halogen or phenyl.

In a preferred embodiment, said $R^7$ is hydrogen, trifluoromethanesulfonyl, methylsulfonyl or p-toluenesulfonyl.

In a preferred embodiment, $R^1$ is hydrogen, $C_{1-6}$ alkyl, $C_{1-6}$ haloalkyl or phenyl.

The extractant of the present invention can be conveniently and easily synthesized at low cost. It can be synthesized by using, for example, Skraup reaction (Schenkel, H.; Schenkel, M *Helv. Chim. Acta*, 1944, 27, 1456), Diels-Alder reaction (Collis, G. E.; Burrell, A. K. *Tetrahedron Lett.* 2005, 46, 3653), Combes reaction (Combes, A. *Bull. Soc. Chim. Fr.* 1988, 49, 89), or Palladium-catalyzed reaction (Piecheowska, J.; Gryko, D. T. *J. Org. Chem.* 2011, 76, 10220).

Extraction Organic Phase

The extraction organic phase of the present invention preferably comprises the extractant of the present invention, a synergic extractant and a diluent.

The extraction organic phase can be used for separating and extracting lithium isotopes;

preferably, the lithium isotopes can be separated from alkaline aqueous phase containing lithium ions, wherein the alkaline aqueous phase containing lithium ions comprises (but not limited to): the mixed water solution of lithium salts (e.g., LiCl, LiBr, LiI, $Li_2SO_4$, $Li_2CO_3$, $LiNO_3$, $Li_3PO_4$, LiSCN, $CF_3COOLi$, LiOH, etc.) and strong alkalis (e.g., sodium hydroxide, etc.). Preferably, the concentration of the lithium salt is 0.01-10 mol/L, preferably 0.1-1.5 mol/L. The concentration of the strong alkali is 0.5-15 mol/L, preferably 2-7 mol/L.

The synergic extractant comprises phosphorus-containing compounds, nitrogen-containing compounds (including quaternary ammonium salts and the like), alkyl quaternary sulfonium salt compounds (the alkyl quaternary sulfonium salt compounds are preferably $C_{1-36}$ alkyl quaternary sulfonium salt compounds; preferably $C_{1-20}$ alkyl quaternary sulfonium salt compounds; more preferably $C_{1-10}$ alkyl quaternary sulfonium salt compounds) or sulfoxide compounds. Preferably, the synergic extractant is neutral phosphorus-containing compounds, quaternary ammonium salt compounds, long-chain alkyl quaternary sulfonium salt compounds or neutral sulfoxide compounds, for example, comprising (but not limited to): tributyl phosphate (TBP), trioctyl-phosphine oxide (TOPO), dibutyl butanephosphonate (DBBP), butyl dibutylphosphate (BDBP), methylene tetrabutyldiphosphate, trioctyl ammonium oxide, 1,10-phenanthroline, quaternary ammonium salt N263, dimethyl bis(N-octadecyl) ammonium chloride, methyldioctylsulfoniumate chloride or dioctyl sulfoxide. Such synergic extractants are easy to solve in organic phase as well as to extract the lithium ions together with the extractant, which can significantly increase the extraction rate. Meanwhile, such synergic extractants can be conveniently obtained from common sources, and their cost is much less than that of hydrophilic ionic liquids. During the process of reverse extraction, the synergic extractant of the present invention can be recovered and regenerated together with the extractant, thereby being recycled and reused.

The diluent comprises (but is not limited to): organic solvents such as kerosene, octanone, chloroform, carbon tetrachloride, toluene, dimethylbenzene, diethylbenzene, bromobenzene, anisole, nitromethane, 2-methyl cyclohexanone, methyl isobutyl ketone, chlorobenzene, dichlorobenzene, trichlorobenzene, diphenyl ether, or the combinations thereof.

Preferably, the concentration of the extractant is 0.01-10 mol/L, preferably 0.1-1 mol/L; and/or the concentration of the synergic extractant is 0.1-10 mol/L, preferably 0.05-2 mol/L.

It should be understood that the extraction organic phase can also comprises certain amount of lithium ions; certainly, the lithium ion is in a small amount so as to not affect the lithium isotope extraction efficiency of the extraction organic phase. Preferably, the content of the lithium ion is 0-2.0 mol/L; more preferably 0.01-0.5 mol/L.

System for Separation of Lithium Isotopes

The present invention provides a system for separating lithium isotopes (or named extraction system or separation system), which comprises an extraction organic phase, and an alkaline aqueous phase containing lithium ions, as described in the present invention.

In a preferred embodiment, the alkaline aqueous phase containing lithium ions is a water solution comprising a lithium salt and a strong alkali.

In a preferred embodiment, the lithium salt comprises (but not limited to) LiCl, LiBr, LiI, $Li_2SO_4$, $Li_2CO_3$, $LiNO_3$, $Li_3PO_4$, LiSCN, $CF_3COOLi$, LiOH, etc.; preferably, the concentration of the lithium salt is 0.01-10 mol/L, preferably 0.1-1.5 mol/L.

In a preferred embodiment, the strong alkali comprises (but not limited to) sodium hydroxide, potassium hydroxide, etc.; the concentration of the strong alkali is 0.5-15 mol/L, preferably 2-7 mol/L.

In a preferred embodiment, the ratio between the extraction organic phase and the aqueous phase comprising lithium ion is 1-10: 1-3 by volume.

Principle of Extraction

The characteristic of the molecular structure of the extractant according to the present invention is that there is a Z—H substitute group on the $10^{th}$ position of benzoquinoline; the "Z—H substitute group" is a hydroxyl group, a mercapto group, or an amino group substituted by $R^9$ (i.e., Z is O, S or $NR^9$). The "Z—H substitute group" has high protonic acidity, and it will lose proton under an alkaline condition and therefore form oxygen anion, sulfur anion or nitrogen anion correspondingly. All the three types of anion can bind to lithium cations, and form strong Z—Li bonds.

During the process of separating lithium isotopes from the alkaline aqueous phase containing lithium ions, the extractant and the lithium ions can form lithium ion chelates (or called "extractant-lithium chelate").

For example, with the assistance of the synergic extractant (L), the extractant and the lithium ion can further form an "extractant-lithium chelate" of formula (IIa) or formula (IIb):

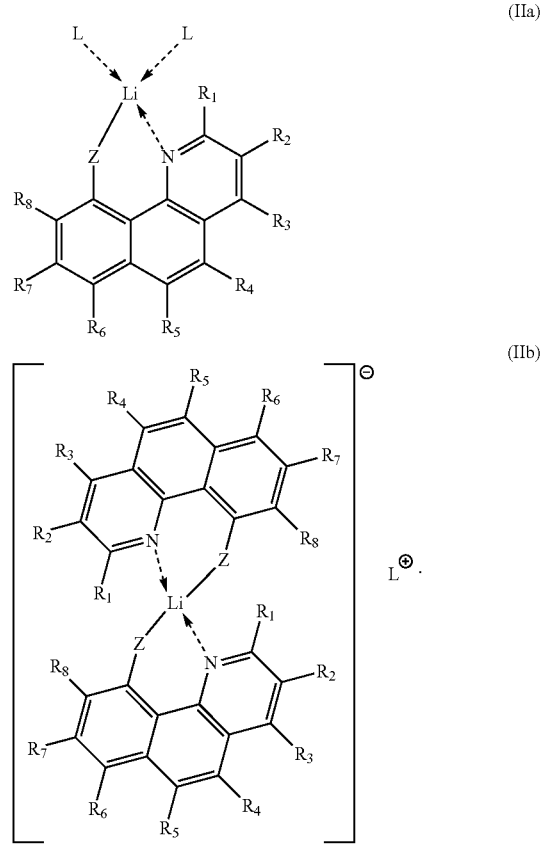

When the synergic extractant (L) is neutral phosphorus-containing compounds, neutral nitrogen-containing compounds or neutral sulfoxide compounds, the extractant, the lithium ion and the synergic extractant will form the lithium ion chelate of formula (IIa); whereas, when the synergic extractant is quaternary ammonium salt type nitrogen-containing compounds or quaternary sulfonium salt compounds, the lithium ion chelate of formula (IIb) will form.

The "extractant-lithium chelate" will go into the organic phase, thus finishing the extraction process.

Said "extractant-lithium chelates" all have strong Z—Li bonds, with the coordination of other assistant atoms, generating very different chemical environment for the lithium isotope ions in the organic phase and the aqueous phase, thus producing significant isotopes separation effect with greater separation coefficient α value. Meanwhile, this strong Z—Li bond results in a rapid isotope exchange process, and easier enrichment of $^7Li$ in the organic phase, thereby facilitating the separation of $^7Li$ and $^6Li$. This has significant difference and improvement when compared to the traditional lithium amalgam separation method.

Extraction Method

The method for separating lithium isotopes as described in the present invention comprises the following steps:

(1) Extracting;

(1.1) providing the extraction organic phase of the present invention;

(1.2) providing an alkaline aqueous phase containing lithium ions; In a preferred embodiment, the alkaline aqueous phase containing lithium ions is a water solution comprising a lithium salt and a strong alkali.

In a preferred embodiment, the lithium salt comprises (but not limited to) LiCl, LiBr, LiI, $Li_2SO_4$, $Li_2CO_3$, $LiNO_3$, $Li_3PO_4$, LiSCN, $CF_3COOLi$, LiOH, etc.; preferably, the concentration of the lithium salt is 0.01-10 mol/L, preferably 0.1-1.5 mol/L.

In a preferred embodiment, the strong alkali comprises (but not limited to) sodium hydroxide, potassium hydroxide, etc.; the concentration of the strong alkali is 0.5-15 mol/L, preferably 2-7 mol/L.

(1.3) mixing the extraction organic phase and the alkaline aqueous phase, stratifying, and collecting the organic phase, said organic phase comprising "extractant-lithium chelate";

Preferably, the ratio between the extraction organic phase and the aqueous phase is 1-10: 1-3 by volume.

Wherein, after the extraction organic phase and the aqueous phase were mixed, the extractant of the extraction organic phase will form an "extractant-lithium chelate" with the lithium ions in the aqueous phase and enter into the organic phase, thus forming an organic phase which comprises the "extractant-lithium chelate".

(2) Reverse Extracting:

Reverse extracting the organic phase comprising the "extractant-lithium chelate" obtained from the preceding steps by using a reverse extractant, and collecting the aqueous phase to obtain the solution with separated and enriched lithium isotopes, and further to obtain the separated lithium isotopes.

Preferably, the ratio between the organic phase comprising the "extractant-lithium chelate" and the reverse extractant is 1-8: 1-10 by volume.

The reverse extractant comprises (but not limited to): water solution of sodium salt (e.g., NaCl, NaBr, NaI, $Na_2SO_4$, $NaNO_3$, etc.), water solution of ammonium salt (e.g., $NH_4Cl$, $(NH_4)_2SO_4$, $NH_4NO_3$, etc.), water solution of potassium salt (e.g., KCl, $K_2SO_4$, etc.).

This reverse extraction procedure is advantageously efficient and fast. The one-time reverse extraction rate is up to 75%, the two-time reverse extraction rate is up to 98% or more, and the three-time reverse extraction rate is up to 99%. The efficiency of reverse extraction is much higher than that reported in CN201110425430.4 wherein the one-time reverse extraction rate is 12% and the fifteen-time reverse extraction rate is 99.1%. The extractant and the synergic extractant can be recycled and reused through the efficient and rapid reverse extraction. The water solution collected after the reverse extraction is the $^7$Li enriched solution.

Single Stage Extraction Separation Experiment

The single stage extraction separation experiment investigated the basic properties of the extractant, i.e., a single extraction provides a separation coefficient α value. The extractant of the present invention has a comparatively high separation coefficient α value which is up to 1.022 or more. Meanwhile, the reverse extractant is mild and pollution-free; it has a high reverse extraction rate; and the extractant and the synergic extractant are easy to be regenerated and recycled through phase inversion.

A preferred single stage extraction separation method comprises the steps of:

1. Extracting;

1.1 providing an extraction organic phase, for example comprising: extractant 0.1-1 mol/L, synergic extractant 0.05-2 mol/L, and dilute which is the aforementioned organic solvent;

1.2 providing an alkaline aqueous phase containing lithium ions, for example comprising: lithium salt 0.1-1.5 mol/L, sodium hydroxide or potassium hydroxide 2-7 mol/L.

1.3 determining the phase ratio between the two phases (e.g., 1-10:1-3), using suitable instruments to obtain samples of the two phases, e.g., using a separating funnel to vibrate for a while (e.g., 1-5 minutes), and stood for a while (e.g., 5 minutes) to layer, thus separating and obtaining samples of the two phases; or alternatively using a high performance centrifugal extractor, continuously charging and discharging the extractor by a flowing ratio of 1-10:1-3, obtaining the two phases at the outlet as the sample.

1.4 Testing the separation coefficient and distribution ratio

Preferably, the ratio of $^7$Li/$^6$Li in the two phases can be determined by inductively coupled plasma-mass spectroscopy, thus calculating the single stage separation coefficient.

Preferably, the concentration of lithium ions in the two phases can be determined by flame photometry, thus calculating the distribution ratio.

2. Reverse Extracting:

Adding the reverse extraction water solution (e.g., 0.1-2 mol/L) to the organic phase, determining the phase ratio of the two phases (e.g., 1-8:1-10), then separating the two phases, reverse extracting for several times (e.g., 2-3 times), thereby the $^7$Li enriched in the organic phase is transferred into the reverse extraction aqueous phase, and the extractant and the synergic extractant are regenerated and recycled.

Multiple Stage Enrichment Process

Multiple stage enrichment process is the only way to achieve multiple-time accumulating enrichment of isotopes. For example, 340 stages of accumulating enrichment are needed under total reflux to enrich 99.995% of $^7$Li product from 92.5% of natural $^7$Li raw material.

The extractant of the present invention is of good chemical stability, and has achieved the repeatedly accumulating enrichment of lithium isotopes, and also significantly reduced the number of stages (or times) of the accumulation. For example, by using 156 mixer-settlers as the extraction equipment, upon a long-time run for 500 hours, multiple stage enriching separation of lithium isotopes was achieved, the abundance of $^7$Li being enriched and raised from 95.60% to 98.47%. Alternatively, by using a centrifugal extractor as the extraction equipment, multiple stage (25 stages) enrichment of lithium isotopes was also achieved, the abundance of $^7$Li being enriched and raised from 92.5% to 95.0%.

The main advantages of the present invention are:

(1) The present invention provides a class of benzoquinoline extractants, and an extraction organic phase which employs the extractant of the present invention, the synergic extractant and the diluent.

There is a Z—H substituent group in the molecular structure of the extractant. Under alkaline condition, with the assistance of a synergic extractant, said extractant is easy to form strong Z—Li bond with lithium ion, thus forming "extractant-lithium chelate". Said extractant is of low toxicity and showed excellent chemical stability in long-time (over 500 hours) single stage or multiple stage extraction separation experiments, and it is easy to be reverse extracted and recycled.

(2) The present invention provides a method of separating lithium isotopes from an alkaline aqueous phase containing lithium ions, said method comprising the steps of extraction and reverse extraction, wherein the reverse extractant is mild and pollution-free, and the reverse extraction process is efficient and rapid, thus saving much of the cost of multiple stage enrichment experiments.

Comparing to the amalgam method which is the only industrialized method, the extraction method of the present invention avoids using mercury which is highly toxic. Therefore, the method of the present invention is friendly to the environment, reduces the cost of lithium isotope separation, and has high economic benefits.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Example 1 Single-Stage Extraction Separation Experiment

Extraction:

Extraction organic phase: extractant: 0.5 mol/L 7-methoxy-10-hydroxy benzoquinoline; synergic extractant: 0.3 mol/L N263; diluent: chloroform.

Aqueous phase: 0.2 mol/L LiCl; 6 mol/L NaOH

Phase ratio: 1:1 (the volume ratio between the organic phase and the aqueous phase) The extraction organic phase and aqueous phase were added into a separating funnel and vibrated for 5 minutes, and then allowed to stand for 5 minutes to stratify. Both phases were collected as the extracted organic phase and the extracted aqueous phase, respectively. Alternatively, a high performance centrifugal extractor was used, and it was continuously charged and discharged at a 1:1 flowing ratio. The two phases were obtained at the exit as the extracted organic phase and the extracted aqueous phase.

It was determined that the $^7$Li/$^6$Li in the extracted organic phase was 14.436, and the $^7$Li/$^6$Li in the extracted aqueous phase was 14.112; that is to say, the separation coefficient α value was 14.436/14.112=1.023.

It was determined that the concentration of the lithium ions in the extracted organic phase was 0.12 mol/L, and that in the extracted aqueous phase was 0.08 mol/L, and the extraction distribution ratio D=0.12/0.08=1.5, i.e., the one-time extraction ratio was 60%.

Reverse Extraction:

The extracted organic phase was reverse extracted by 1 mol/L NaCl water solution (reverse extractant), and the phase ratio was 1:1 (the volume ratio between the extracted organic phase and the reverse extraction aqueous phase). The reverse extraction was conducted for three times. The $^7$Li enriched in the extracted organic phase transferred into the reverse extraction aqueous phase, and the extractant and the synergic extractant was thus allowed to be regenerated and recycled. The three-time reverse extraction rate was measured to be 99%.

Example 2 Single-Stage Extraction Separation Experiment

Extraction:

The method of extraction was the same with example 1, but the following conditions were employed:

Extraction organic phase: extractant: 0.3 mol/L 10-hydroxy benzoquinoline; synergic extractant: 0.6 mol/L trioctylphosphine oxide (TOPO); diluent: dichlorobenzene.

Aqueous phase: 0.2 mol/L LiCl; 4 mol/L NaOH
Phase ratio: 2:1

The extraction distribution ratio was measured to be D=1.6, i.e. the one-time extraction rate was 62% and the single-stage separation coefficient α=1.022.

Reverse Extraction:

The reverse extraction method was the same with Example 1, but the reverse extractant employed was 1 mol/L $Na_2SO_4$;

The three-time reverse extraction rate was measured to be 99%.

Example 3 Single-Stage Extraction Separation Experiment

Extraction:

The method of extraction was the same with example 1, but the following conditions were employed:

Extraction organic phase: extractant: 0.4 mol/L 10-hydroxy benzoquinoline; synergic extractant: 0.3 mol/L quaternary ammonium salt N263; diluent: trichlorobenzene.

Aqueous phase: 0.2 mol/L LiCl; 4.8 mol/L NaOH
Phase ratio: 1:1

The extraction distribution ratio was measured to be D=1.7, i.e. the one-time extraction rate was 63% and the single-stage separation coefficient α=1.022.

Reverse Extraction:

The reverse extraction method was the same with Example 1, but the reverse extractant employed was 1 mol/L $NH_4Cl$;

The three-time reverse extraction rate was 99%.

Example 4 Single-Stage Extraction Separation Experiment

Extraction:

The method of extraction was the same with example 1, but the following conditions were employed:

Extraction organic phase: extractant: 0.6 mol/L 2,4-dimethyl-10-hydroxy benzoquinoline; synergic extractant: 1.0 mol/L trioctylphosphine oxide (TOPO); diluent: octanone.

Aqueous phase: 0.2 mol/L LiCl; 4 mol/L KOH
Phase ratio: 2:1

The extraction distribution ratio was measured to be D=1.1, i.e. the one-time extraction rate was 52% and the single-stage separation coefficient α=1.023.

Reverse Extraction:

The reverse extraction method was the same with Example 1, but the reverse extractant employed was 1 mol/L $NH_4Cl$;

The three-time reverse extraction rate was 99%.

Example 5 Single-Stage Extraction Separation Experiment

Extraction:

The method of extraction was the same with example 1, but the following conditions were employed:

Extraction organic phase: extractant: 0.4 mol/L 9-propyl-10-hydroxy benzoquinoline; synergic extractant: 0.8 mol/L N263; diluent: dichlorobenzene.

Aqueous phase: 0.2 mol/L LiCl; 5 mol/L NaOH
Phase ratio: 1:1

The extraction distribution ratio was measured to be D=1.4, i.e. the one-time extraction rate was 58% and the single-stage separation coefficient α=1.023.

Reverse Extraction:

The reverse extraction method was the same with Example 1, but the reverse extractant employed was 1 mol/L $NH_4Cl$;

The three-time reverse extraction rate was 99%.

Example 6 Single-Stage Extraction Separation Experiment

Extraction:

The method of extraction was the same with example 1, but the following conditions were employed:

Extraction organic phase: extractant: 0.4 mol/L 9-isobutyl-10-hydroxy benzoquinoline; synergic extractant: 0.8 mol/L dimethyl di(N-octadecyl) ammonium chloride; diluent: dichlorobenzene.

Aqueous phase: 0.2 mol/L $Li_2SO_4$; 5 mol/L KOH
Phase ratio: 3:1

The extraction distribution ratio was measured to be D=0.8, i.e. the one-time extraction rate was 44% and the single-stage separation coefficient α=1.024.

Reverse Extraction:

The reverse extraction method was the same with Example 1, but the reverse extractant employed was 1 mol/L $NH_4Cl$;

The three-time reverse extraction rate was 99%.

Example 7 Single-Stage Extraction Separation Experiment

Extraction:

The method of extraction was the same with example 1, but the following conditions were employed:

Extraction organic phase: extractant: 0.4 mol/L 7-trifluoromethyl-10-hydroxy benzoquinoline; synergic extractant: 0.8 mol/L quaternary ammonium salt N263; diluent: dichlorobenzene.

Aqueous phase: 0.2 mol/L LiCl; 5 mol/L NaOH
Phase ratio: 1:1

The extraction distribution ratio was measured to be D=1.9, i.e. the one-time extraction rate was 66% and the single-stage separation coefficient α=1.025.

Reverse Extraction:

The reverse extraction method was the same with Example 1, but the reverse extractant employed was 1 mol/L NH$_4$Cl;

The three-time reverse extraction rate was 99%.

Example 8 Single-Stage Extraction Separation Experiment

Extraction:

The method of extraction was the same with example 1, but the following conditions were employed:

Extraction organic phase: extractant: 0.4 mol/L 5-chloro-10-hydroxy benzoquinoline; synergic extractant: 0.8 mol/L methyldioctylsulfonium chloride; diluent: dichlorobenzene.

Aqueous phase: 0.2 mol/L LiCl; 5 mol/L NaOH

Phase ratio: 1:1

The extraction distribution ratio was measured to be D=1.6, i.e. the one-time extraction rate was 62% and the single-stage separation coefficient α=1.023.

Reverse Extraction:

The reverse extraction method was the same with Example 1, but the reverse extractant employed was 1 mol/L (NH$_4$)$_2$SO$_4$;

The three-time reverse extraction rate was 99%.

Example 9 Single-Stage Extraction Separation Experiment

Extraction:

The method of extraction was the same with example 1, but the following conditions were employed:

Extraction organic phase: extractant: 0.4 mol/L 5-fluoro-9-methoxy-10-hydroxy benzoquinoline; synergic extractant: 0.8 mol/L N263; diluent: dichlorobenzene.

Aqueous phase: 0.2 mol/L LiCl; 5 mol/L KOH

Phase ratio: 1:1

The extraction distribution ratio was measured to be D=1.5, i.e. the one-time extraction rate was 60% and the single-stage separation coefficient α=1.028.

Reverse Extraction:

The reverse extraction method was the same with Example 1, but the reverse extractant employed was 1 mol/L (NH$_4$)$_2$SO$_4$;

The three-time reverse extraction rate was 99%.

Example 10 Single-Stage Extraction Experiment

Extraction:

The method of extraction was the same with example 1, but the following conditions were employed:

Extraction organic phase: extractant: 0.4 mol/L 6-methyl-7-bromo-10-mercapto benzoquinoline; synergic extractant: 0.4 mol/L N263; diluent: trichlorobenzene.

Aqueous phase: 0.2 mol/L LiCl; 5 mol/L NaOH

Phase ratio: 1:1

The extraction distribution ratio was measured to be D=0.7, i.e. the one-time extraction rate was 42% and the single-stage separation coefficient α=1.022.

Reverse Extraction:

The reverse extraction method was the same with Example 1, but the reverse extractant employed was 1 mol/L NH$_4$Cl;

The three-time reverse extraction rate was 99%.

Example 11 Single-Stage Extraction Separation Experiment

Extraction:

The method of extraction was the same with example 1, but the following conditions were employed:

Extraction organic phase: extractant: 0.4 mol/L 10-(N-trifluoromethylsulfonyl)amino-benzoquinoline; synergic extractant: 1.0 mol/L butyl dibutylphosphate (BDBP); diluent: dichlorobenzene.

Aqueous phase: 0.2 mol/L LiCl; 5 mol/L NaOH

Phase ratio: 3:1

The extraction distribution ratio was measured to be D=1.5, i.e. the one-time extraction rate was 60% and the single-stage separation coefficient α=1.023.

Reverse Extraction:

The reverse extraction method was the same with Example 1, but the reverse extractant employed was 1 mol/L NH$_4$Cl;

The three-time reverse extraction rate was 99%.

Example 12 Four-Stage Counter Current Extraction Experiment

The following conditions were employed:

Extraction organic phase: extractant: 0.5 mol/L 6-methyl-10-hydroxy benzoquinoline; synergic extractant: 0.3 mol/L N263; diluent: dichlorobenzene.

Aqueous phase: 0.6 mol/L LiCl; 5 mol/L NaOH

Phase ratio: 3.8:1

A four-stage counter current extraction experiment was conducted to comprehensively study the extraction performance of the extractant. After the four-stage counter current extraction, the concentration of lithium in the aqueous phase was less than 2.5*10$^{-4}$ mol/L, with the extraction rate being up to 99.96%, thus realizing the efficient extraction of lithium ions.

The result of the extraction is shown in Table 1.

TABLE 1

| Extraction stages | Concentration of lithium in the aqueous phase | Concentration of lithium in the organic phase |
| --- | --- | --- |
| 1 | 2.5*10$^{-4}$ mol/L | 2.5*10$^{-4}$ mol/L |
| 2 | 2.8*10$^{-3}$ mol/L | 0.025 mol/L |
| 3 | 0.016 mol/L | 0.097 mol/L |
| 4 | 0.44 mol/L | 0.18 mol/L |

Example 13 8-Stage Counter Current Extraction Experiment

The following conditions were employed:

Extraction organic phase: extractant: 0.5 mol/L 10-hydroxy benzoquinoline; synergic extractant: 0.3 mol/L methyldioctylsulfonium chloride; diluent: dichlorobenzene.

Aqueous phase: 0.62 mol/L LiCl; 5.2 mol/L NaOH

Phase ratio: 3.6:1

An eight-stage counter current extraction experiment was conducted to comprehensively study the extraction performance of the extractant. After the eight-stage counter current extraction experiment, the concentration of lithium in aqueous phase was less than 8.2*10$^{-5}$ mol/L, with the extraction rate being up to 99.99%, thus realizing the efficient extraction of lithium ions.

The extraction balance line is shown in FIG. 1.

Example 14 25-Stage Lithium Isotope Enrichment Process Experiment Using Centrifugal Extractor The following conditions were employed:

Extraction organic phase: extractant: 0.5 mol/L 6-methyl-10-hydroxy benzoquinoline; synergic extractant: 0.3 mol/L methyldioctylsulfonium chloride; diluent: dichlorobenzene.

Aqueous phase: 0.6 mol/L $Li_2SO_4$; 5 mol/L NaOH

Flowing ratio: 3.8:1

A 25-stage lithium isotope enrichment process experiment using a centrifugal extractor was conducted to comprehensively study numerous performances of the extractant, such as extraction, enrichment, and reverse extraction. After a long time testing and running, it was found that the extractant has good chemical stability, and the multi-stage enrichment and separation of lithium isotopes was achieved, with the abundance of $^7Li$ isotope raising to 95.0% after enrichment from the original abundance of 92.5%.

In conclusion:

The separation system of lithium isotopes of the present invention has a high distribution ratio (D value) of lithium ions (which can reach up to 1.9); the first-time extraction rate can reach up to 66%, which is far more higher than that of the first-time extraction ratio of the organic phase reported in CN201110425430.4 (about 15.2%-19.0%); the extraction organic phase is easy to enrich $^7Li$ and has a high separation coefficient (which can reach up to 1.028), which is remarkably superior to the other existing solvent extraction systems (usually <1.010); And the multiple stage enrichment of lithium isotopes has been achieved.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. An extraction organic phase for separating lithium isotopes, wherein said extraction organic phase comprises: a diluent, and the compound of formula (I) used as an extractant:

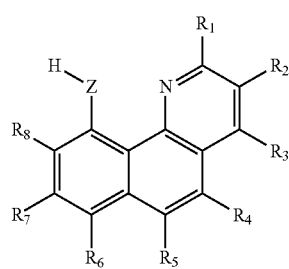

(I)

wherein,

Z is oxygen atom, sulfur atom, or nitrogen atom substituted by $R^9$, wherein $R^9$ is hydrogen, $C_{1-6}$ alkyl-sulfonyl, $C_{1-6}$ haloalkyl-sulfonyl, benzenesulfonyl or $C_{1-6}$ alkyl-benzenesulfonyl;

$R^1$, $R^2$, $R^3$, $R^4$, $R^5$, $R^6$, $R^7$ and $R^8$ are independently hydrogen, $C_{1-6}$ alkyl, $C_{1-6}$ haloalkyl, $C_{2-6}$ alkenyl, $C_{2-6}$ alkynyl, $C_{1-6}$ alkoxy, $C_{3-6}$ cycloalkyl, halogen or phenyl.

2. The extraction organic phase of claim 1, wherein the extraction organic phase further comprises a synergic extractant.

3. The extraction organic phase of claim 2, wherein the synergic extractant is phosphorus-containing compounds, nitrogen-containing compounds, alkyl quaternary sulfonium salt compounds or sulfoxide compounds.

4. The extraction organic phase of claim 3, wherein the synergic extractant comprises: tributyl phosphate (TBP), trioctyl-phosphine oxide (TOPO), dibutyl butanephosphonate (DBBP), butyl dibutylphosphate (BDBP), methylene tetrabutyldiphosphate, trioctyl ammonium oxide, 1,10-phenanthroline, quaternary ammonium salt N263, dimethyl bis (N-octadecyl) ammonium chloride, methyldioctylsulfonium chloride or dioctyl sulfoxide.

5. The extraction organic phase of claim 1, wherein the diluent comprises: kerosene, octanone, chloroform, carbon tetrachloride, toluene, dimethylbenzene, diethylbenzene, bromobenzene, anisole, nitromethane, 2-methyl cyclohexanone, methyl isobutyl ketone, chlorobenzene, dichlorobenzene, trichlorobenzene, diphenyl ether, or a combination thereof.

6. The extraction organic phase of claim 1, wherein the extraction organic phase further comprises lithium ions.

7. A composition for separating lithium isotopes, wherein said composition comprises the extraction organic phase of claim 1, and an alkaline aqueous phase containing lithium ions.

8. The composition of claim 7, wherein the lithium ions comprise $^7Li$ and $^6Li$.

9. A method for separating lithium isotopes from an alkaline aqueous phase containing lithium ions, wherein said method comprises the steps of:

mixing the extraction organic phase of claim 1 with an alkaline aqueous phase containing lithium ions to form a mixture;

stratifying the mixture, and collecting an organic phase therefrom, wherein the organic phase comprises: a synergic extractant, lithium ion, and the extractant:

reverse extracting the collected organic phase with an extractant, and collecting an aqueous phase, which comprises separated lithium isotopes.

* * * * *